(12) United States Patent
Sablone et al.

(10) Patent No.: US 10,849,796 B2
(45) Date of Patent: Dec. 1, 2020

(54) APPARATUS AND METHOD FOR MANUFACTURING ABSORBENT CORES

(71) Applicant: Fameccanica.Data S.p.A., Pescara (IT)

(72) Inventors: Gabriele Sablone, Pescara (IT); Antonio Cappucci, Carpineto della Nora (IT); Antonio Giansante, Spoltore (IT); Alessandro Cipriani, Teramo (IT)

(73) Assignee: FAMECCANICA.DATA S.P.A., San Giovanni Teatino (IT)

( * ) Notice: Subject to any disclaimer, the term of this patent is extended or adjusted under 35 U.S.C. 154(b) by 56 days.

(21) Appl. No.: 16/163,722

(22) Filed: Oct. 18, 2018

(65) Prior Publication Data

US 2019/0142649 A1 May 16, 2019

(30) Foreign Application Priority Data

Oct. 20, 2017 (IT) .................. 102017000119095

(51) Int. Cl.
*A61F 13/532* (2006.01)
*A61F 13/15* (2006.01)
(Continued)

(52) U.S. Cl.
CPC .... *A61F 13/1565* (2013.01); *A61F 13/15617* (2013.01); *A61F 13/15642* (2013.01);
(Continued)

(58) Field of Classification Search
None
See application file for complete search history.

(56) References Cited

U.S. PATENT DOCUMENTS

| 5,494,622 A * | 2/1996 | Heath ............... A61F 13/15658 156/276 |
| 2006/0021695 A1* | 2/2006 | Blessing ........... A61F 13/15658 156/196 |

(Continued)

FOREIGN PATENT DOCUMENTS

| EP | 2873397 A1 | 5/2015 |
| WO | 2017171777 A1 | 10/2017 |

OTHER PUBLICATIONS

Italian Search Report and Written Opinion dated May 11, 2018 for Application No. IT201700119095.

*Primary Examiner* — Jeffry H Aftergut
(74) *Attorney, Agent, or Firm* — Patterson + Sheridan, LLP

(57) ABSTRACT

An apparatus for manufacturing absorbent cores for absorbent sanitary articles, comprising: a rotating forming wheel including a plurality of forming elements defining a peripheral surface of the forming wheel, a forming chamber containing absorbent material facing a portion of the peripheral surface of the forming wheel, a first roller for feeding a first nonwoven web onto the peripheral surface of the forming wheel upstream of the forming chamber, a second roller for feeding a second nonwoven web onto the peripheral surface of the forming wheel downstream of the forming chamber, wherein each of said forming elements comprises a suction surface connected to a suction source and at least one protruding rib having a blowing surface selectively connected to a stationary blowing device, wherein said at least one blowing surface and said suction surface are spaced apart from each other in a radial direction.

9 Claims, 4 Drawing Sheets

(51) Int. Cl.
   *A61F 13/539* (2006.01)
   *A61F 13/534* (2006.01)

(52) U.S. Cl.
   CPC ...... *A61F 13/15699* (2013.01); *A61F 13/539* (2013.01); *A61F 13/5323* (2013.01); *A61F 13/15585* (2013.01); *A61F 13/534* (2013.01)

(56) References Cited

U.S. PATENT DOCUMENTS

2013/0284361 A1* 10/2013 Tsujimoto ................. B32B 5/16
                                                    156/276
2015/0144270 A1*  5/2015 Nakakado ........... A61F 13/5323
                                                    156/580.2
2016/0346805 A1* 12/2016 McNeil ................ B05C 1/0808

* cited by examiner

APPARATUS AND METHOD FOR MANUFACTURING ABSORBENT CORES

FIELD OF THE INVENTION

The present invention refers to the manufacture of absorbent sanitary articles and relates to an apparatus and a method for manufacturing absorbent cores containing an absorbent material formed by superabsorbent polymers in powder form and/or cellulose fibers.

DESCRIPTION OF THE PRIOR ART

Absorbent cores for absorbent sanitary articles may comprise absorbent material based on cellulose fluff, and/or superabsorbent polymers in powder form, enclosed between two nonwoven webs welded together along their perimeter.

Absorbent sanitary articles are increasingly common on the market, in which the absorbent material has a high percentage of super-absorbent powdered polymers. In some cases the absorbent material is almost exclusively composed of superabsorbent polymers in powder form.

In certain cases, the production of absorbent cores is required that have one or more channels without absorbent material located within the absorbent core. The object of these channels is to promote the distribution of body fluids along a larger area of the absorbent core to improve absorption characteristics. These channels may also have the function of promoting the folding of the absorbent core and of improving the adaptability of the absorbent sanitary products to the user's body.

To ensure that the channels without absorbent material do not disappear during the production method, it is necessary to isolate the channels from the surrounding areas of the absorbent core containing the absorbent material. Isolation of the channels from the absorbent material can be made by fastening the two nonwoven webs along the perimeter of the channels, for example, by gluing or welding. Joining the two nonwoven webs in internal areas of the absorbent core is problematic since any contamination of the joining surfaces with absorbent material can render the joint ineffective.

In the state-of-the-art, various solutions have already been proposed for joining two webs of an absorbent core. Examples of the known solutions are described in EP-A-2764141, EP-A-2674140, and U.S. Pat. No. 7,524,449.

The solutions according to the prior art do not solve the problem of joining two webs of nonwoven fabric inside an area containing absorbent material, while avoiding contamination of the joining surfaces by the absorbent material, especially in the case in which the absorbent material consists mainly or exclusively of superabsorbent powder.

OBJECT AND SUMMARY

The present invention aims to provide a method and an apparatus that satisfies the aforesaid needs and that overcomes the problems of the prior art According to the present invention, this object is achieved by a method and apparatus having the characteristics described here.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

It will be appreciated that for simplicity and clarity of illustration, the figures are not represented on the same scale.

DETAILED DESCRIPTION

Figure 1:
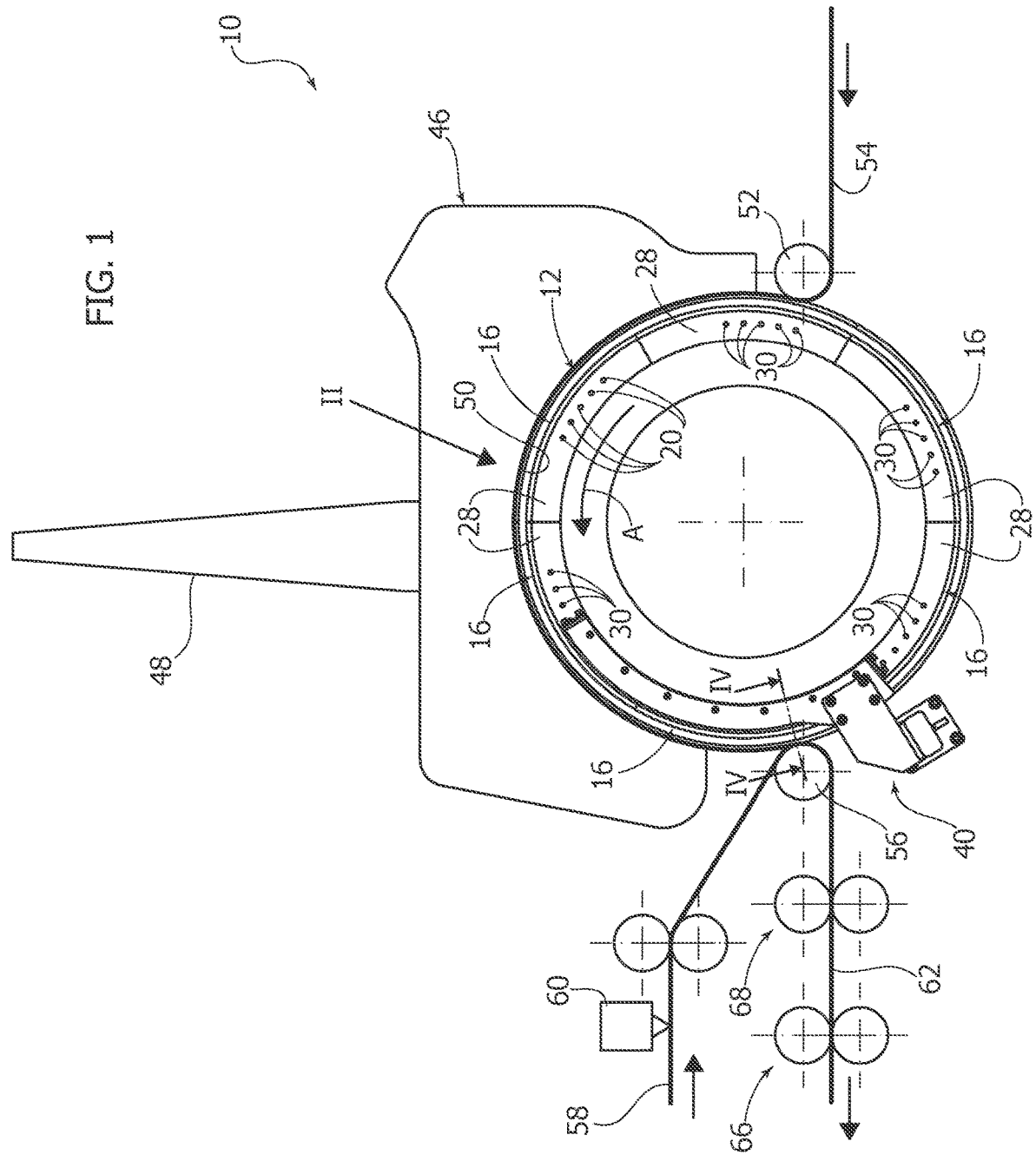
FIG. 1 is a schematic view of an apparatus for producing absorbent cores according to the present invention.

With reference to FIG. 1, numeral 10 indicates an apparatus for producing absorbent cores for absorbent sanitary articles. The apparatus 10 comprises a forming wheel 12 rotatable about its axis in the direction indicated by the arrow A in FIG. 1.

Figure 2:
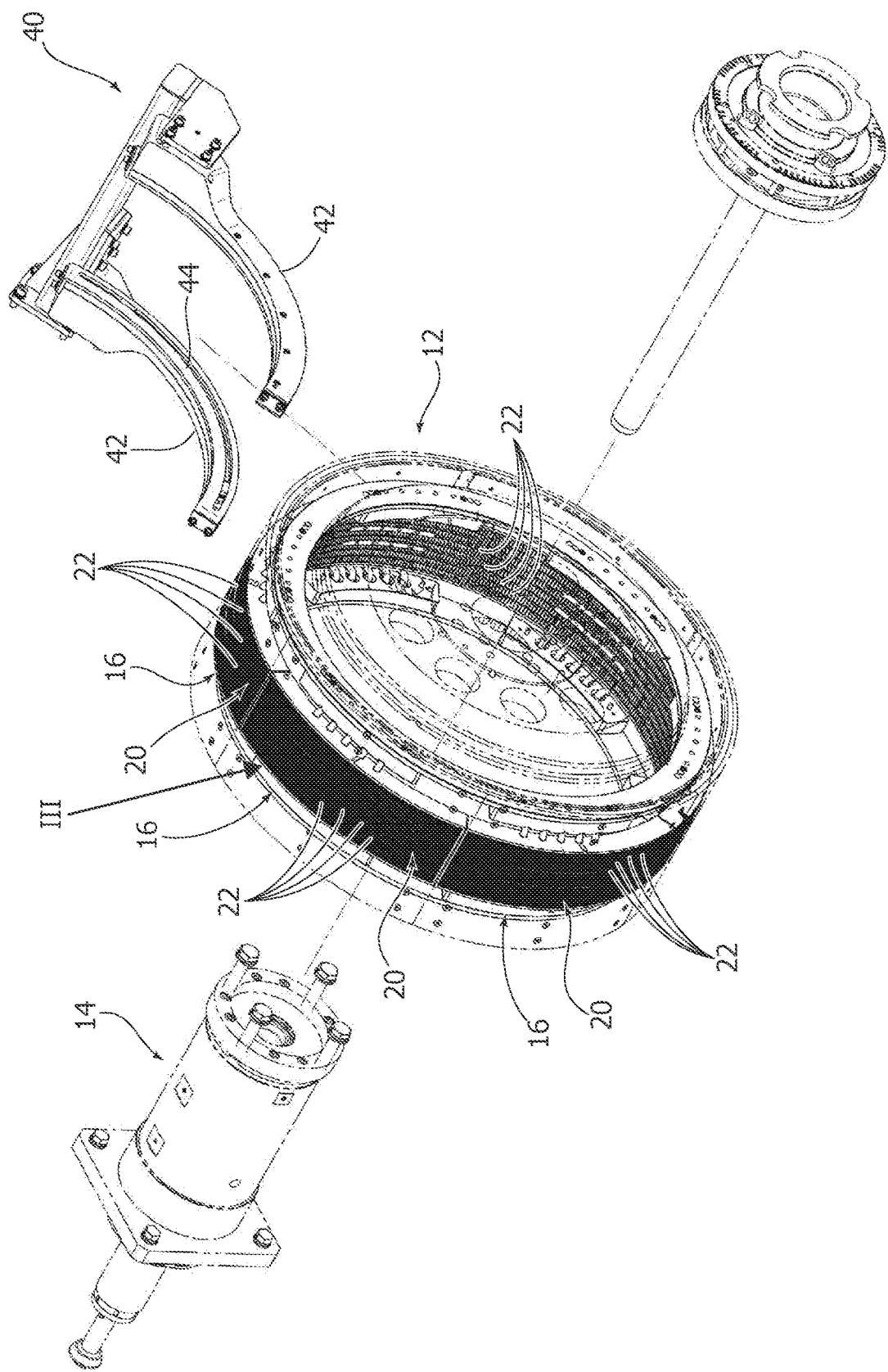
FIG. 2 is an exploded perspective view of the part indicated by the arrow II in FIG. 1.
Figure 3:
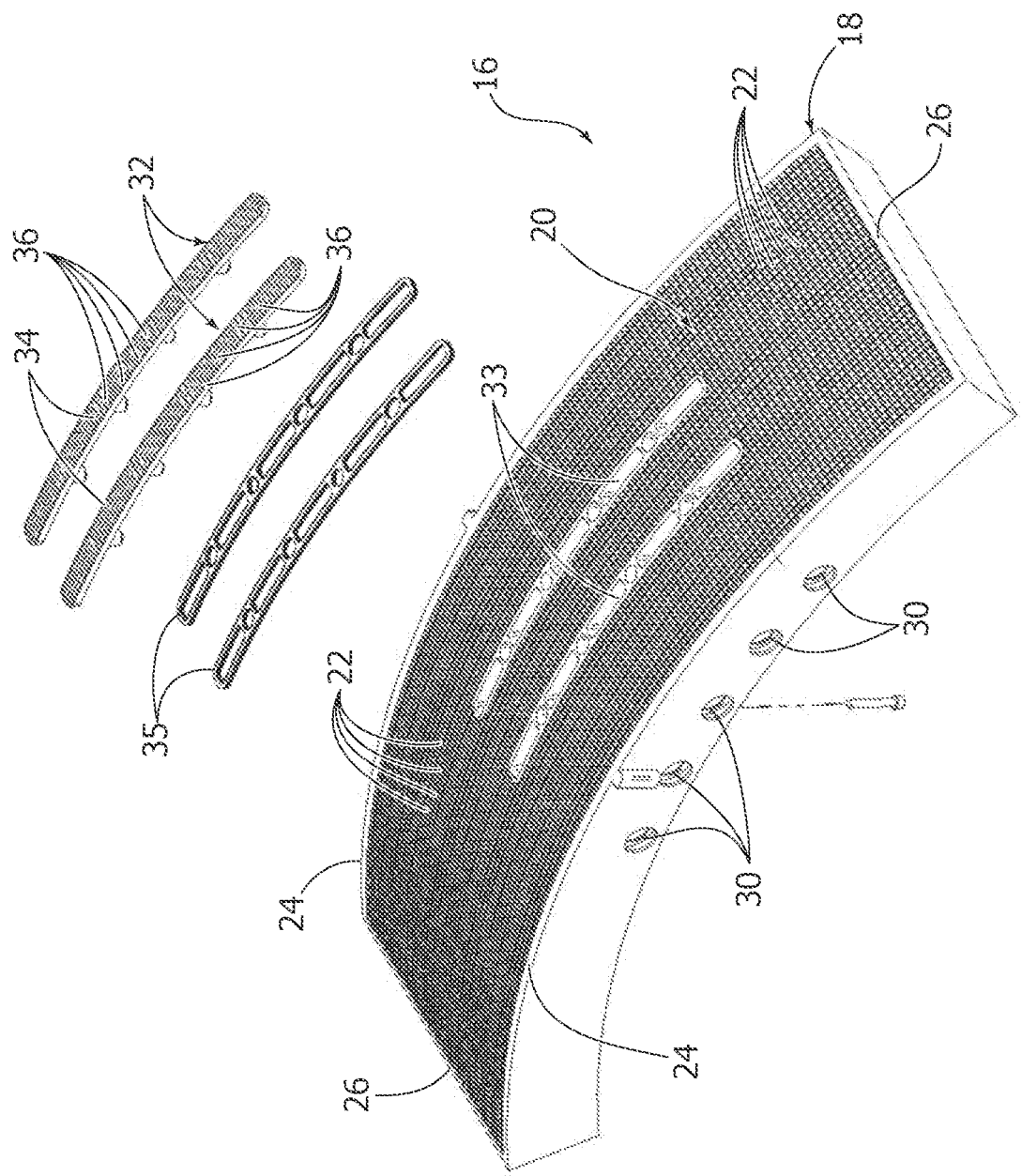
FIG. 3 is an exploded perspective view of a forming element indicated by the arrow III in FIG. 2.

With reference to FIG. 2, a stationary manifold 14 connected to a vacuum source is arranged inside the forming wheel 12. The forming wheel 12 comprises a plurality of forming elements 16 defining the peripheral surface of the forming wheel 12. The forming elements 16 are intended to form respective absorbent cores. With reference to FIG. 3, each forming element 16 comprises a body 18 substantially having the shape of a cylindrical sector, having the shape and dimensions corresponding to those of the absorbent cores which are produced by the apparatus 10. The body 18 of each forming element 16 can be obtained by 3-D printing of polymeric material.

The body 18 of each forming element 16 has a bottom wall 20 with a convex cylindrical shape, provided with a multitude of suction holes 22 connected to the vacuum source.

Figure 4:
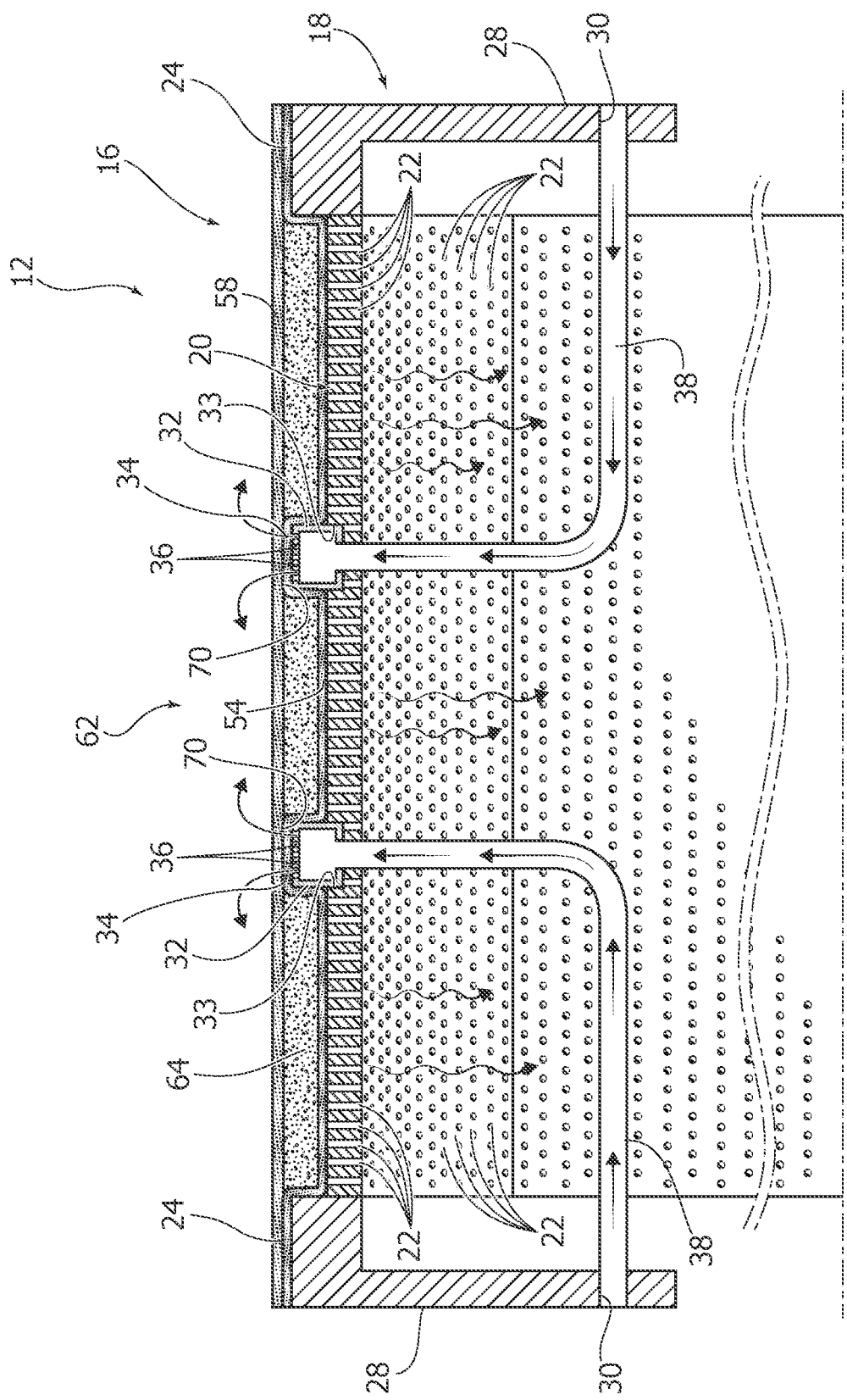
FIG. 4 is a schematic cross-sectional view according to the line IV-IV of FIG. 1, illustrating a step in the process of forming an absorbent core.

The body 18 of each forming element 16 comprises two longitudinal edges 24 and two transverse edges 26, raised with respect to the bottom wall 20. The body 18 has two parallel sides 28 provided with holes 30. On each front side of the forming wheel 12, the sides 28 of the various forming elements 16 are contained in a common plane, perpendicular to the rotation axis of the forming wheel 12. Each forming element 16 comprises one or more ribs 32 projecting from the bottom wall 20 of the body 18. The ribs 32 may be separate elements from the body 18 fastened within respective grooves 33, or can be integrally formed with the body 18. In the illustrated example, two parallel ribs 32 are provided, oriented parallel to the longitudinal direction (machine direction). In the illustrated example, spacer elements 35 are provided, arranged between the ribs 32 and the body 18, which allow adjustment of the projection height of the ribs 32. The ribs 32 have respective head surfaces 34 provided with a multitude of blowing holes 36 connected to the holes 30 formed on the sides 28 of the body 18 by means of channels 38 (FIG. 4).

With reference to FIGS. 1 and 2, the apparatus 10 comprises a stationary blowing device 40 connected to a source of pressurized air. The blowing device 40 comprises at least one arm 42 for supplying pressurized air. In the illustrated example, the blowing device 40 comprises two arched arms 42 having respective grooves 44 for the outlet of pressurized air. The two arms 42 face respective sides 28 of the forming elements 16. The pressurized air delivered by the blowing device 40 enters the holes 30 of the forming elements 16 which, from time to time, face the arms 42 of the blowing device 40. The pressurized air coming from the blowing device 40 exits through the holes 36 of the protruding ribs 32. Blowing of air through the holes 36 only occurs when the holes 30 of the forming elements 16 are facing the arms 42 of the stationary blowing device 40.

With reference to FIG. 1, the apparatus 10 comprises a stationary forming chamber 46 containing absorbent material consisting of superabsorbent powdered material and/or cellulose fluff. A duct 48 can be provided for feeding the absorbent material to the forming chamber 46. The forming chamber 46 has an outlet opening 50 facing the peripheral surface of the forming wheel 12.

The apparatus 10 comprises a first roller 52 which feeds a first web of nonwoven fabric 54 upstream of the forming chamber 46. The first nonwoven web 54 is fed to the peripheral surface of the forming wheel 12 at the same peripheral speed of the forming wheel 12.

The apparatus 10 comprises a second roller 56 that feeds a second nonwoven web 58 onto the peripheral surface of the forming wheel 12 downstream of the forming chamber 46. The second nonwoven web 58 is also fed to the peripheral surface of the forming wheel 12 at the same peripheral speed of the forming wheel 12.

The apparatus 10 may comprise a glue dispenser 60 for applying glue to the second nonwoven web 58 upstream of the second roller 56. The second roller 56 can feed the second nonwoven web 58 onto the peripheral surface of the forming wheel 12 and, at the same time, detach—from the forming wheel 12—the composite tape 62 formed by the two nonwoven webs 54, 56 which enclose a layer of absorbent material 64 (FIG. 4).

With reference to FIG. 1, the apparatus 10 may comprise a welding unit 66 which creates a weld on the composite tape 62, which joins together the two nonwoven webs 54, 58 along longitudinal and transversal lines that define the perimeter of the absorbent cores. The welding unit 66 can also carry out welding between the two nonwoven webs 54, 58 along internal areas of the composite web 62 without absorbent material. A pressing unit 68 can be provided upstream of the welding unit 66.

With reference to FIGS. 3 and 4, each forming element 16 comprises a suction area formed by the bottom wall 20 of the body 18 and a blowing area formed by the head surfaces 34 of the protruding ribs 32. The suction surface 20 and the blowing surfaces 34 are spaced apart in a radial direction with respect to the rotation axis of the forming wheel 12. The blowing surfaces 34 are entirely contained within the suction surface 20. Additional blowing surfaces could also be provided along the longitudinal edges 24 and along the transverse edges 26 of the forming element 16. The suction surface 20 has the object of retaining the absorbent material 64 on the forming element 16. The blowing surfaces 34 are designed to form channels 70 (FIG. 4) without absorbent material inside the absorbent cores. The channels 70 are entirely surrounded by absorbent material 64. The channels 70 can be elongated along a longitudinal direction (machine direction). The absorbent cores may have two channels 70 parallel to each other, which have the function of distributing the liquids inside the absorbent core to facilitate the absorption of the liquids by the absorbent material 64. The channels without absorbent material 70 may also have the function of facilitating the folding of the absorbent core, to allow better adaptation of the absorbent core to the user's body.

With reference to FIGS. 1 and 4, the first nonwoven web 54 is fed onto the peripheral surface of the forming wheel 12 upstream of the forming chamber 46, and is placed directly in contact with the suction surfaces 20 of the forming elements 16. The first nonwoven web 54 is raised from the suction surface 20 at the protruding ribs 32. During rotation of the forming wheel 12, the forming elements 16 face the forming chamber 46. The first nonwoven web 54 is permeable to air. Therefore, when the forming elements 16 face the forming chamber 46, the flow of air sucked through the holes 22 of the forming elements 16 retains the absorbent material 64 on the first nonwoven web 54 at the suction surface 20.

After having applied the absorbent material 64 onto the first nonwoven web 54, during rotation of the forming wheel 12, the forming elements 16 are positioned at the arms 42 of the blowing device 40. In this condition, a flow of air is blown through the holes 36 of the blowing surfaces 34 of the protruding ribs 32. The blowing of air through the blowing surfaces 34 can take place simultaneously with the intake of air through the suction surface 20. The blowing of air exiting through the holes 36 of the blowing surfaces 34 removes any traces of absorbent material from the areas of the first nonwoven web located at the protruding ribs 32. The blowing of air through the blowing surfaces 34 can continue even after the forming elements 16 leave the forming chamber 46.

Downstream of the forming chamber 46, the second nonwoven web 58 is fed onto the peripheral surface of the forming wheel 12, and is arranged above the absorbent material 64. Applying the second nonwoven web 58 can be carried out while air is blown through the blowing surfaces 34 of the protruding ribs 32. The glue applied to the second nonwoven web 58, prior to applying the second nonwoven web 58 onto the peripheral surface of the forming wheel 12, enables the second nonwoven web 58 to adhere to the first nonwoven web 54 along the longitudinal and transverse edges 24, 26 and along the protruding ribs 32 of the forming elements 16.

Downstream of the application area of the second nonwoven web 58, a composite structure is obtained, schematically illustrated in FIG. 4, in which channels 70 without absorbent material are formed at the protruding ribs 32. The contact area between the two nonwoven webs 54, 58 at the protruding ribs 32 is free from contamination by the absorbent material. Thus, the two webs of nonwoven fabric 54, 58 can be fastened together at the channels 70 by means of glue and/or welding, avoiding contamination by the absorbent material 64 in the joining areas between the two webs 54, 58. The fact that the blowing surfaces 34 and the suction surfaces 20 are spaced apart allows a more effective cleaning of the joining areas, and more effectively avoids contamination by absorbent material dust particles.

Of course, without prejudice to the principle of the invention, the details of construction and the embodiments may be widely varied with respect to those described and illustrated, without thereby departing from the scope of the invention as defined by the claims that follow.

The invention claimed is:

1. A method for manufacturing absorbent cores for absorbent sanitary articles, comprising:
   providing a rotating forming wheel including a plurality of forming elements defining a peripheral surface of the forming wheel, each of the forming elements comprising at least one protruding rib inserted into a respective groove formed on a suction surface of the respective forming element,
   providing a forming chamber containing absorbent material facing a portion of the forming wheel;
   feeding a first nonwoven web onto the peripheral surface of the forming wheel upstream of the forming chamber;
   retaining absorbent material on said first nonwoven web at the suction surfaces of the forming elements connected to a suction source;

blowing air through blowing surfaces of the protruding ribs, the blowing surfaces being spaced apart radially from respective suction surfaces;

feeding a second nonwoven web onto the forming wheel over the absorbent material; and fastening together the first and second nonwoven webs along channels without absorbent material formed by the blowing surfaces.

2. A method according to claim 1, wherein the blowing of air through the blowing surfaces is carried out simultaneously with the suction through the suction surfaces.

3. A method according to claim 1, wherein applying the second nonwoven web to the forming wheel is carried out while air is blown through the blowing surfaces.

4. A method according to claim 1, wherein glue is applied to the second nonwoven web prior to feeding the second nonwoven web onto the forming wheel.

5. A method according to claim 1, comprising welding the first and second nonwoven webs along perimeter lines of absorbent cores and along channels without absorbent material surrounded by absorbent material.

6. An apparatus for manufacturing absorbent cores for absorbent sanitary articles, comprising:

a rotating forming wheel including a plurality of forming elements defining a peripheral surface of the forming wheel;

a forming chamber containing absorbent material facing a portion of the peripheral surface of the forming wheel;

a first roller for feeding a first nonwoven web onto the peripheral surface of the forming wheel upstream of the forming chamber; and a second roller for feeding a second nonwoven web onto the peripheral surface of the forming wheel downstream of the forming chamber, wherein each of the forming elements comprises a suction surface connected to a suction source, and at least one protruding rib having a blowing surface selectively connected to a stationary blowing device, wherein:

the at least one blowing surface and the suction surface are spaced apart from each other in a radial direction, and the protruding rib is inserted into a respective groove formed on the suction surface of the respective forming element.

7. An apparatus according to claim 6, wherein each of the forming elements comprises at least one side provided with holes selectively facing a respective arm of the stationary blowing device, the holes being connected to the blowing surface by means of channels.

8. An apparatus according to claim 6, wherein the forming elements are formed by 3-D printing.

9. An apparatus according to claim 6, wherein at least one spacer element is arranged between the protruding rib and said groove to adjust the height of the blowing surface with respect to the suction surface.

* * * * *